United States Patent
Tandai

(10) Patent No.: US 9,881,365 B2
(45) Date of Patent: Jan. 30, 2018

(54) SEMICONDUCTOR DEFECT CATEGORIZATION DEVICE AND PROGRAM FOR SEMICONDUCTOR DEFECT CATEGORIZATION DEVICE

(71) Applicant: HITACHI HIGH-TECHNOLOGIES CORPORATION, Tokyo (JP)

(72) Inventor: Yutaka Tandai, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 123 days.

(21) Appl. No.: 14/395,999

(22) PCT Filed: Apr. 11, 2013

(86) PCT No.: PCT/JP2013/060939
§ 371 (c)(1),
(2) Date: Oct. 21, 2014

(87) PCT Pub. No.: WO2013/161577
PCT Pub. Date: Oct. 31, 2013

(65) Prior Publication Data
US 2015/0213596 A1 Jul. 30, 2015

(30) Foreign Application Priority Data

Apr. 23, 2012 (JP) ................................ 2012-097793

(51) Int. Cl.
*G06K 9/00* (2006.01)
*G06T 7/00* (2017.01)
(Continued)

(52) U.S. Cl.
CPC ....... *G06T 7/0006* (2013.01); *G01N 21/8851* (2013.01); *G01N 21/9501* (2013.01); *G01N 21/956* (2013.01); *G06K 9/6268* (2013.01); *G06T 7/001* (2013.01); *G06T 7/0008* (2013.01); *H01L 22/12* (2013.01);
(Continued)

(58) Field of Classification Search
None
See application file for complete search history.

(56) References Cited

U.S. PATENT DOCUMENTS

2006/0169896 A1* 8/2006 Ataka ............... G03F 1/68
250/310
2007/0053583 A1 3/2007 Harabe
(Continued)

FOREIGN PATENT DOCUMENTS

JP 2006-0215077 A 8/2006
JP 2007-102153 A 4/2007
(Continued)

OTHER PUBLICATIONS

International Search Report issued in Application No. PCT/JP2013/060939 dated Jul. 2, 2013.
(Continued)

*Primary Examiner* — Fred Hu
(74) *Attorney, Agent, or Firm* — McDermott Will & Emery LLP

(57) ABSTRACT

The present invention provides semiconductor defect classification equipment for classifying a defect in a semiconductor wafer. The semiconductor defect classification equipment is provided with: a display unit; a storage unit that stores an inspection image including an inspection object portion on the semiconductor wafer and design data of the semiconductor wafer including a plurality of manufacturing steps; and an processing unit that displays the inspection image and the design data on the display unit. The processing unit acquires at least one first layout data and the inspection image from the storage unit, and displays the first layout data and the inspection image on the display unit in a superposed manner.

4 Claims, 10 Drawing Sheets

(51) Int. Cl.
   *H01L 21/66* (2006.01)
   *G01N 21/88* (2006.01)
   *G01N 21/95* (2006.01)
   *G01N 21/956* (2006.01)
   *G06K 9/62* (2006.01)
   *H01L 21/67* (2006.01)

(52) U.S. Cl.
   CPC ...... *G01N 2201/12* (2013.01); *G06T 2200/24* (2013.01); *G06T 2207/10004* (2013.01); *G06T 2207/30148* (2013.01); *H01L 21/67288* (2013.01); *H01L 2924/0002* (2013.01)

(56) References Cited

U.S. PATENT DOCUMENTS

| | | | |
|---|---|---|---|
| 2012/0131529 A1* | 5/2012 | Hayakawa | G01N 21/95607 716/112 |
| 2013/0084655 A1* | 4/2013 | Yue | G03F 7/70633 438/7 |

FOREIGN PATENT DOCUMENTS

| | | |
|---|---|---|
| JP | 2009-10286 A | 1/2009 |
| WO | 2011-004534 A1 | 1/2011 |
| WO | WO 2011004534 A1 * | 1/2011 ......... G01N 21/8851 |

OTHER PUBLICATIONS

Office Action issued in corresponding Japanese Patent Application No. 2012-097793, dated May 10, 2016.

* cited by examiner

Fig. 2

[INFORMATION]
~ Omitted ~
Image magnification ratio (low ratio)=8000
Image magnification ratio (high ratio)=15000
Image resolution (low ratio)=512
Image resolution (high ratio)=512
  .
  .
[RESULT]
Defect area center of gravity X coordinates=230.000
Defect area center of gravity Y coordinates=235.500

```
[LAYER_INFORMATION]
DisplayLayoutCount=2
DisplayLayout1=abc
CadLayerCount=2
CadLayer1=1,0
CadLayer2=2,200
    .
    .
DisplayLayout2=efg
CadLayerCount=3
CadLayer1=5,0
CadLayer2=7,2
CadLayer3=8,0
    .
    .
[LayoutPara]
MainLayout=2
CorrdinatesOffsetX=123456.123
CorrdinatesOffsetY=123456.123
    .
    .
[LayoutOffset]
offset1=23.123 , 0.234
    .
    .
```
~20

SEMICONDUCTOR DEFECT CATEGORIZATION DEVICE AND PROGRAM FOR SEMICONDUCTOR DEFECT CATEGORIZATION DEVICE

CROSS-REFERENCE TO RELATED APPLICATIONS

The present application is the U.S. National Phase of PCT/JP2013/060939 filed Nov. 4, 2013, which claims priority to Japanese Patent Application No. 2012-097793 filed Apr. 23, 2012. The disclosures of the above applications are incorporated herein by reference.

TECHNICAL FIELD

The present invention relates to semiconductor defect classification equipment for classifying defects including a systematic defect in a wafer or chip during semiconductor device design evaluation process or manufacturing process.

BACKGROUND ART

Decreases in the manufacturing yield of semiconductor devices have been considered mainly due to randomly caused defects, such as foreign matter or impurity. The yield has been maintained by searching for relevant factors using a defect inspection device or a defect review device, and then implementing a countermeasure in a manufacturing step. However, in recent years, the minimum pattern line width of semiconductor devices has become smaller from 32 nm to 22 nm and is advancing toward 10× nm with an accompanying increase in the ratio of defects depending on design data.

A defect having design dependency is referred to as a "systematic defect". The systematic defect includes, for example, resistance abnormality caused by a pattern shape variation due to an underlying height difference, and contact hole conduction failure due to insufficient etching of a gate oxide film in a specific area.

In order to decrease semiconductor wafer defects, inspection is performed during the manufacture of the wafer using various defect inspection devices, such as a dark-field system, a bright-field system, or an electron beam system. Based on defect position information detected by these defect inspection devices, a clear image of a defect is acquired by a review device. Based on the acquired image, the defect is automatically classified by automatic defect classification (ADC), and a defect countermeasure is taken in accordance with the category and frequency of the classified defect.

However, the conventional ADC technology merely classifies the defect into a category according to the shape and brightness and the like of the defect observed in the review device, and is not capable of clarifying the cause of the defect. The cause of a systematic defect in some cases may be analyzed based on the manner in which layers are superposed in a manufacturing step, or the manner in which a plurality of steps is implemented in a specific layer (such as for multiple patterning). Thus, recently, there is a demand for a technology for classifying defects using the design data for each step.

Conventionally, there have already been attempts to associate a defect with design data. For example, Patent Literature 1 describes that "using layout design data corresponding to a layer currently formed on a device to be inspected and an upper or lower layer formed on the current layer, the defect classification definition unit 221 defines a defect classification area on the surface of the device to be inspected." Patent Literature 1 further describes that "the defect classification process unit 222, with regard to sampling defect data 133 (233) sampled from a defect acquired by the defect review device 10, classifies the defect depending on in which area of the defined area the position of the defect is included."

CITED LITERATURE

Patent Literature

Patent Literature 1: JP 2009-10286 A

SUMMARY OF INVENTION

Technical Problem

In the conventional technology according to Patent Literature 1, a defect is classified merely according to which area of the area defined using the layout design data the defect position is included in. The technology is not capable of sufficiently analyzing the factors causing a defect due to the manner of overlap of layers, or the manner of implementation of a plurality of steps (such as for multiple patterning) in a specific layer.

The present invention provides a technology for analyzing factors causing a systematic defect due to the manner of superposition of layers or the manner of implementation of a plurality of steps in a specific layer, using information of design data.

Solution to Problem

The present invention provides semiconductor defect classification equipment for classifying a defect in a semiconductor wafer, the equipment including a display unit; a storage unit that stores an inspection image including an inspection object portion on the semiconductor wafer, and design data of the semiconductor wafer including a plurality of manufacturing steps; and an processing unit that displays the inspection image and the design data on the display unit. The storage unit stores the design data as a plurality of first layout data divided for each manufacturing step. The processing unit acquires at least one of the first layout data and the inspection image from the storage unit, and displays the first layout data and the inspection image on the display unit in a superposed manner.

Advantageous Effects of Invention

According to the present invention, the inspection image and the design data are displayed on the display unit in a superposed manner, making it possible, with respect to a defect portion, to refer to the manner of superposition of layers or the manner of implementation of a plurality of steps in a specific layer. In this way, factors causing a systematic defect can be analyzed based on information of the design data.

Additional features of the present invention will become apparent from the following description of the present specification and the attached drawings. Problems, configurations, and effects other than those mentioned above will become apparent from the following description of embodiments.

BRIEF DESCRIPTION OF DRAWINGS

FIG. 2 illustrates an example of an image information file according to the embodiment of the present invention.

FIG. 3 illustrates an example of a design data information file according to the embodiment of the present invention.

DESCRIPTION OF EMBODIMENTS

In the following, an embodiment of the present invention will be described with reference to the drawings. While the attached drawings illustrate a specific embodiment and implementation examples in accordance with the principle of the present invention, these are for facilitating an understanding of the present invention and not to be taken for the purpose of interpreting the present invention in a limiting sense.

<Configuration of Semiconductor Defect Inspection System>

Figure 1:
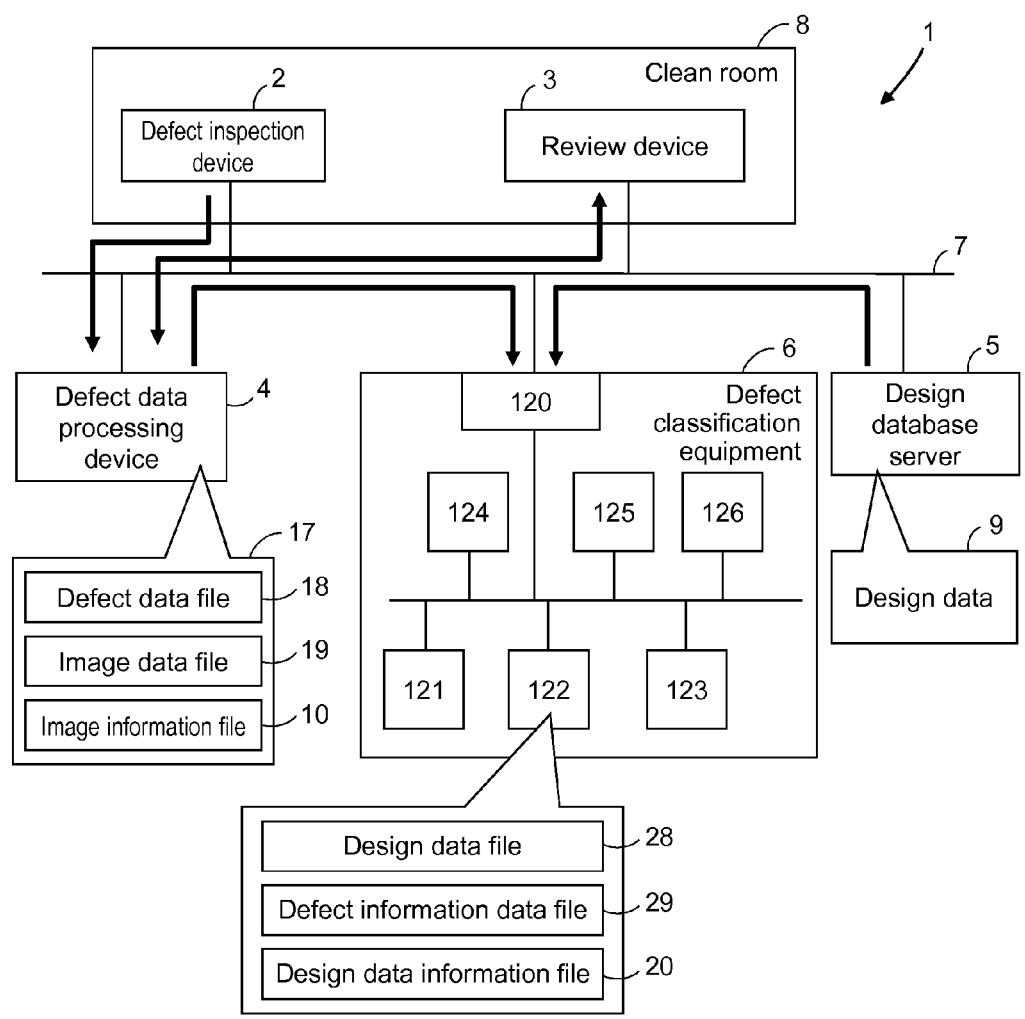
FIG. 1 is an overall configuration diagram of a semiconductor defect inspection system according to an embodiment of the present invention.

FIG. 1 is an overall configuration diagram of a semiconductor defect inspection system according to an embodiment of the present invention. The semiconductor defect inspection system 1 of the present embodiment includes a defect inspection device 2, a review device 3, a defect data processing device 4, a design database server 5, and defect classification equipment 6. The defect inspection device 2, the review device 3, the defect data processing device 4, the design database server 5, and the defect classification equipment 6 are connected via a network 7 enabling mutual data transmission and reception.

A semiconductor manufacturing step includes various steps (not shown), such as impurity injection, film forming, and etching, and is implemented in a clean room 8 in which a clean environment is maintained given the requirement for microfabrication. In the clean room 8 are installed the defect inspection device 2, which inspects a semiconductor wafer for defect, and the review device 3, which performs defect observation based on coordinates on the semiconductor wafer.

The defect inspection device 2 may include, e.g., a dark-field defect inspection device, a bright-field defect inspection device, or an electron beam defect inspection device. The defect inspection device 2 detects a defect caused on the surface of a device to be inspected. The defect inspection device 2 is also provided with the function of acquiring an observation image of the detected defect.

The review device 3 may include a scanning electron microscope (SEM) and the like. The review device 3 acquires a detailed review image of the defect based on coordinate information of the defect, detected by the inspection device 2, on the semiconductor wafer.

The defect data processing device 4 receives various data acquired by the defect inspection device 2 and the review device 3 and the like via the network 7, and manages the data as defect information data 17. The defect information data 17 is stored in a storage device, not shown, of the defect data processing device 4, for example. The defect information data 17 includes a defect data file 18, an image data file 19, and an image information file 10. The defect data processing device 4 receives the defect information data 17 acquired by the defect inspection device 2 and the defect information data 17 acquired by the review device 3 each via the network 7, and manages the respective data.

The defect data file 18 is a file that stores defect identification information identifying the defect detected by the defect inspection device 2, and defect data, such as defect position coordinates of the position of the defect that are determined with respect to a predetermined reference point (origin) provided on each die (chip) and that are expressed on a coordinate system on the die, defect size, and defect factor category.

The image data file 19 is a file that stores the data of the defect image acquired by the defect inspection device 2 having a review function or the review device 3. The image information file 10 is a file that is created corresponding to each image data file 19, and that stores information indicating a status of acquisition of each image data file 19. The details of the image information file 10 will be described later.

The design database server 5 stores design data 9 of a semiconductor wafer manufactured in a predetermined semiconductor manufacturing step. The design data 9 includes design data concerning physical arrangements of elements or wires of the semiconductor device, and also data defining the shape of a mask (mask pattern) used in each manufacturing step. For example, the design data 9 may be defined as a plurality of manufacturing steps (layers) or the type of semiconductor wafer.

In the current semiconductor manufacturing processes, the design data 9 may require a gigantic file capacity as a result of semiconductor process miniaturization, and the file capacity may exceed several dozen gigabytes even for a single design data in each manufacturing step, making handling difficult. As a feature of the present implementation example, the design database server 5 stores the design data 9 in a divided manner. The design data 9 is divided for each layer of the manufacturing step (such as for one manufacturing step). When a plurality of process steps (such as lithography process) are performed to generate a pattern for one layer (hereafter referred to as "multiple patterning"), the design data 9 may be divided for each process step. Further, the design data 9 may be divided for each type of semiconductor wafer.

The defect classification equipment 6 acquires the defect information data 17 of the semiconductor wafer as the object for inspection from the defect data processing device 4 and the design data 9 of the semiconductor wafer from the design database server 5, and displays their images in a superposed manner.

The defect classification equipment 6 may include an information processing device such as a workstation or a personal computer. The defect classification equipment 6 includes a communication unit (network interface) 120, a processing unit 121, a storage unit 122, a layout conversion operating unit 123, a classification determination definition unit 124, a defect determination unit 125, and a user interface 126. While the defect classification equipment 6 is described as having a hardware configuration, its various functions may be realized by a software program code configured to be executed by the processing unit 121 (CPU) of the defect classification equipment 6.

The communication unit 120 is an interface for exchanging data between the defect data processing device 4 and the design database server 5. The processing unit 121 may include a central processing unit (CPU) or a microprocessor and the like, and executes processes for controlling various other units.

The storage unit 122 may include a volatile memory such as a random access memory (RAM), a non-volatile memory such as a flash memory, or a storage device such as a hard disk device. The storage unit 122 stores the defect information data 17 transmitted from the defect data processing device 4 as a defect information data file 29. The storage unit 122 also stores the design data 9 transmitted from the design database server 5 as a design data file 28. The storage unit 122 also stores a design data information file 20 illustrated in FIG. 3. The details of the design data information file 20 will be described later.

The layout conversion operating unit 123 executes a figure conversion process so that the design data 9 transmitted from the design database server 5 can be read into the system. The classification determination definition unit 124 receives defect classification information input from the user interface 126, and defines a classification result for the defect information. The defect determination unit 125 compares a defect image (inspection image) included in the defect information data file 29 with a reference image to extract a defect position from the defect image.

The user interface 126 includes an input device such as a keyboard, a mouse, or various buttons, and an output device such as a liquid crystal display (LCD) device or a printer. The result from the defect classification equipment 6 is displayed on the output device, and an input from an operator is received by the input device.

<Configuration of Image Information File 10>

FIG. 2 illustrates an example of the image information file according to the embodiment of the present invention.

The image information file 10 includes information about the defect image included in the image data file 19, such as an image magnification ratio (low magnification ratio, high magnification ratio), image resolution (low magnification ratio, high magnification ratio), the coordinates of a defect area containing a defect, the coordinates of the center of gravity of the defect area, and the number of superposed frame images constituting the image.

The image magnification ratio of the defect image here is the magnification ratio of the defect image at the time of acquisition of the defect image by the defect inspection device 2 or the review device 3. Normally, the magnification ratio of the defect image is determined by, e.g., a minimum pattern size according to the design rule of the semiconductor device, the size of the defect (defect size) that affects the manufacturing yield of the semiconductor device, and the magnification ratio (FOV: field of view) at which the defect can be contained in the field of view. When layout data included in the design data file 28 and the defect image included in the defect information data file 29 are superposed, the magnification ratio of the defect image is determined at the time of acquisition of the defect image. Thus, by using the magnification ratio information of each defect included in the image information file 10, the magnification ratios of the defect image and the layout data can be aligned.

<Configuration of Design Data Information File 20>

FIG. 3 illustrates an example of the design information file according to the embodiment of the present invention. In the present implementation example, the layout data included in the design data file 28 is divided for each layer of the manufacturing step, or for each process step (such as the lithography step). The design data information file 20 defines, e.g., information about a combination of the divided layout data, and layout data offset information.

For example, the design data information file 20 includes parameters such as the number of display layouts utilized for a display, the configuration of design layers constituting a display layout, the amount of offset (error information) of each display layout, and the amount of enlargement/reduction of a pattern at the time of display of each display layout. Thus, a display layout configuration can be set and configured using a plurality of layout data and the like. Because the parameter of the amount of enlargement/reduction of the pattern at the time of displaying each display layout is included, the defect image and the layout data can be displayed in a superposed manner at high accuracy with respect to an actual pattern. As described above, the design data information file 20 includes, as superposition information for superposition of the layout data, at least one of the amount of offset of each display layout, the amount of enlargement/reduction of the displayed pattern and the like. The amount of offset of the display layout may include error information between layers (first superposition information) and error information between lithography steps (second superposition information). Thus, a display can be made while correcting an error between manufacturing steps or an error between lithography steps in the case of multiple patterning.

<Process Content of Defect Classification Equipment>

Figure 4:
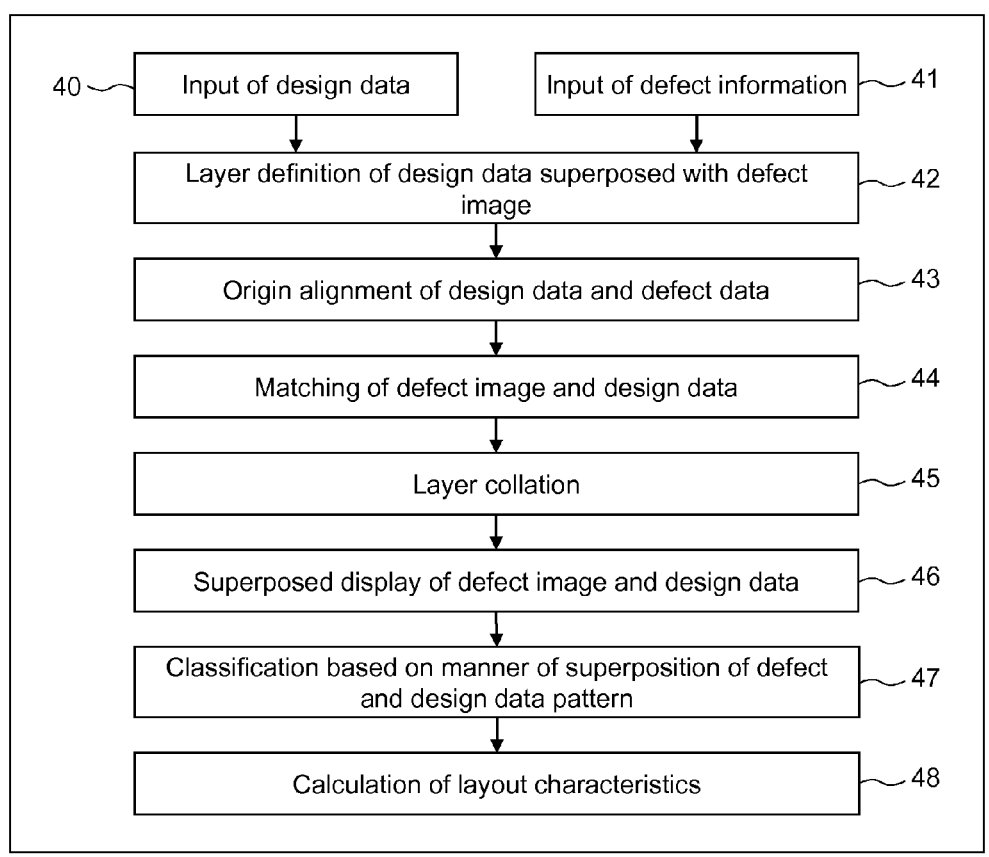
FIG. 4 is a flow chart illustrating the flow of a process in defect classification equipment according to the embodiment of the invention.

FIG. 4 is a flowchart illustrating the flow of a process in the defect classification equipment according to the embodiment of the invention.

First, in step 40, the layout conversion operating unit 123 acquires the layout data included in the design data file 28. Simultaneously, in step 41, the layout conversion operating unit 123 acquires the defect image included in the defect information data file 29. Then, the layout conversion operating unit 123 executes the figure conversion and format conversion processes.

Then, in step 42, the processing unit 121 executes a process of defining the layout data displayed with the defect image in a superposed manner. The processing unit 121, using the parameters of the design data information file 20, defines the layout data displayed with the defect image in a superposed manner. As described above, the layout data in some cases may be defined by a plurality of lithography steps even though the steps relate to one step, as in the case of multiple patterning. For example, the processing unit 121, using the parameters of the design data information file 20, combines the layout data corresponding to a plurality of lithography steps as one inspection object layer while associating the data with each other.

Each of the divided layout data is provided with a layer number corresponding to the layer and with data type information of the semiconductor wafer as the inspection object. In the design data information file 20, the respective layer numbers and the like are associated with each other, and a plurality of steps is defined as one inspection object.

Thus, the operator can handle a plurality of steps as one inspection object without being aware of the plurality of layer numbers or the data type on the user interface 126.

Next, in step 43, the processing unit 121 aligns the origin and magnification ratio between the layout data and the defect image. The layout data may have the origin at the center, while the defect image may have the origin at the lower left of the die, or the respective data may have different coordinate systems. Thus, in step 43, origin alignment is performed. Further, because the magnification ratio may be different between the layout data and the defect image, magnification ratio alignment is also performed.

In step 44, the processing unit 121 executes a matching process between the layout data and the defect image. Because the coordinate systems and the magnification ratios are aligned in step 43, the layout data corresponding to the coordinate position of the defect can be readily obtained based on the coordinate position. However, the coordinate position data often includes an error at the time of defect detection, resulting in a slight position error between the layout data and the defect image. Thus, in this step, pattern matching is performed between the layout data and the defect image in a wider range than the field of view of the defect image.

In step 45, the processing unit 121 performs collation between an inspection object layer and an arbitrary layer. For example, the processing unit 121 receives an input from the user interface 126 and collates the layout data of an input layer. Thus, a layer that could provide a defect factor can be selected from layers under the layer having a defect and collated. Here, a plurality of layers may be selected for one inspection object layer.

Next, in step 46, the processing unit 121 displays the defect image and the layout data on the display device of the user interface 126 in a superposed manner. While not shown in FIG. 4, the defect image displayed here is the image of the defect position extracted by comparing the defect image with the reference image in the defect determination unit 125.

In step 47, the operator, referring to the superposed image displayed on the display device of the user interface 126, inputs defect classification information using the input device. The classification determination definition unit 124 receives the defect classification information inputted by the input device, and defines a classification result for the defect on the defect image.

In step 48, the processing unit 121 identifies the defect position from the layout data and the defect image, and executes a process of calculating the defect density, areal ratio, size and the like of the layer pattern. Finally, a calculation result is displayed on the display device in the form of a parsing result graph, assisting the determination as to whether the defect is a systematic defect.

Figure 5:
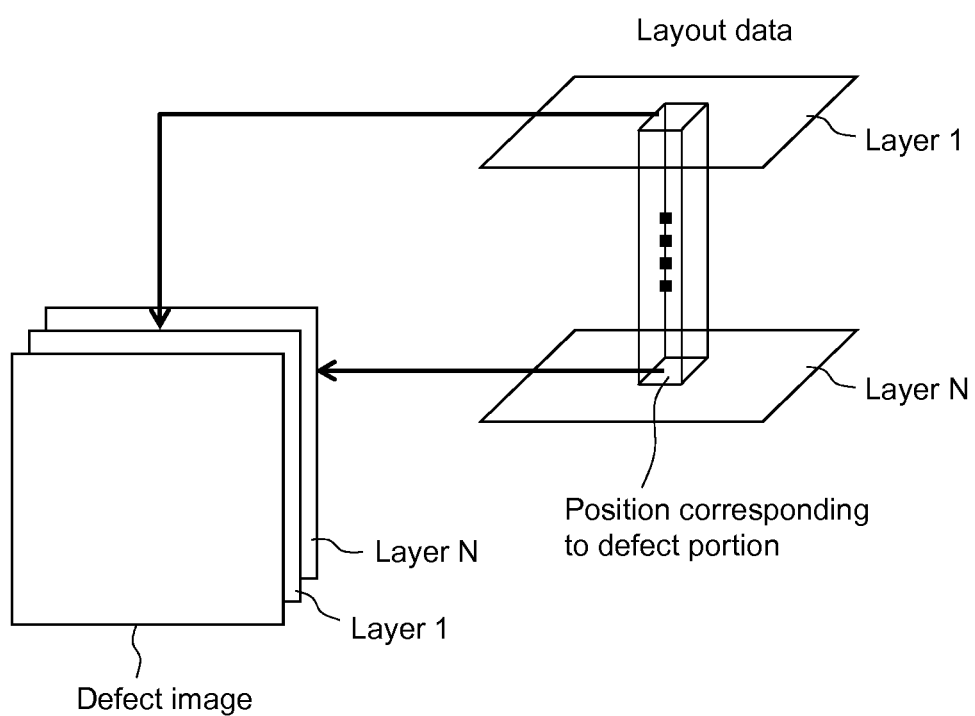
FIG. 5 is a diagram for describing a layout data collating process and a process for displaying a defect image and layout data in a superposed manner.

FIG. 5 is a conceptual diagram of the layer collating process and the superposed display process. As illustrated, a layer that could provide a defect factor is selected from a plurality of layout data divided on a layer by layer (manufacturing step) basis, and collation is performed. At this time, a portion of the layout data corresponding to the defect position of the defect image is acquired. As illustrated in FIG. 5, the same portion corresponding to the defect position is acquired between a plurality of layers (layer 1 and layer N), and the defect image and the layer 1 and the layer N are displayed in a superposed manner on the display device. Superposition information (such as the amount of offset) of the plurality of layers may be acquired from the design data information file 20 to correct an error between the plurality of layers when displayed.

<Display Process in the Case of Multiple Patterning>

Figure 6:
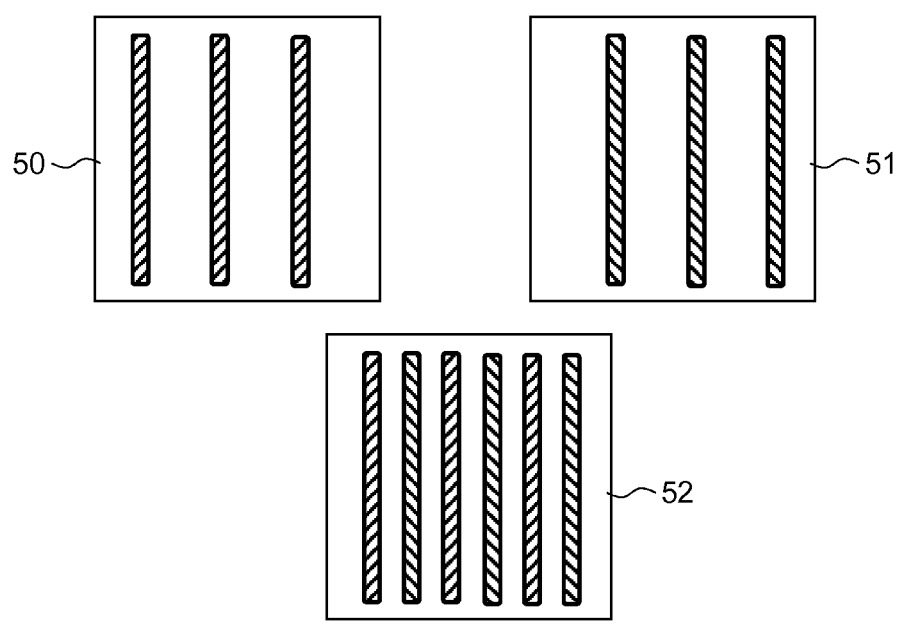
FIG. 6 illustrates a step of generating a pattern by multiple patterning.

A display process in which one manufacturing step is defined by a plurality of process steps, such as in the case of multiple patterning, will be described. FIG. 6 illustrates a step of generating a pattern in a certain specific layer by multiple patterning. In this layer example, first pattern generation 50 is implemented, and then second pattern generation 51 is implemented. Finally, an intended pattern 52 is generated.

Figure 7:
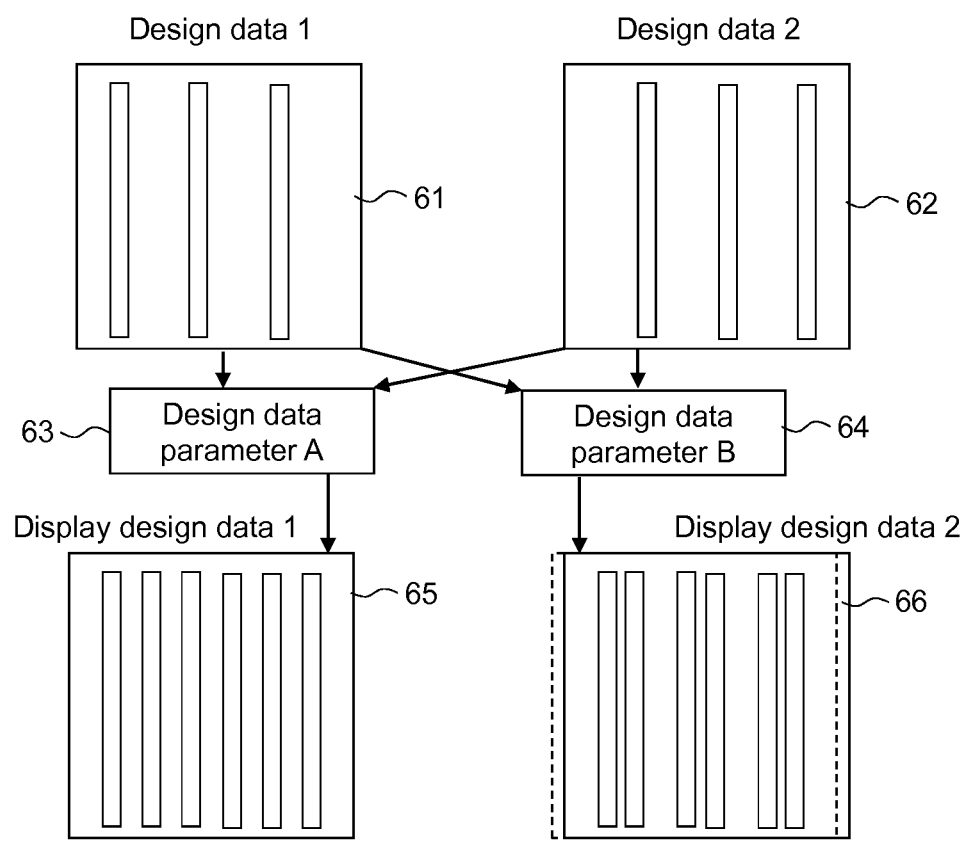
FIG. 7 illustrates a case in which a plurality of layout data is superposed using a plurality of parameters in multiple patterning.

FIG. 7 illustrates a case in which a plurality of layout data are superposed using a plurality of parameters.

In the present implementation example, the design data 9 is stored while being divided for each pattern generation step. One layer is defined by a pattern 61 for first design data (1) and a pattern 62 for second design data (2). As the superposition information, two parameters A (63) and B (64) are set. The result of superposing the two patterns 61 and 62 using the parameter A (63) is a superposition result 65. The result of superposing the two patterns 61 and 62 using the parameter B (64) is a superposition result 66.

The two parameters 63 and 64 may be defined in the design information file 20. In this case, the processing unit 121 acquires the two parameters 63 and 64 from the design data information file 20 as the superposition information, and displays the inspection image and the layout data reflecting the superposition information on the display device in a superposed manner. The two parameters may be input by the operator rather than acquired from the design data information file 20. A parameter range may be set in advance, and the processing unit 121 may calculate a plurality of parameters at predetermined numerical value intervals automatically. Further, information of a plurality of parameters may be stored in the storage unit 122 in advance and subsequently updated by feeding a parameter that the operator deems appropriate after the superposed display back to the parameter information stored in the storage unit 122.

Figure 8:
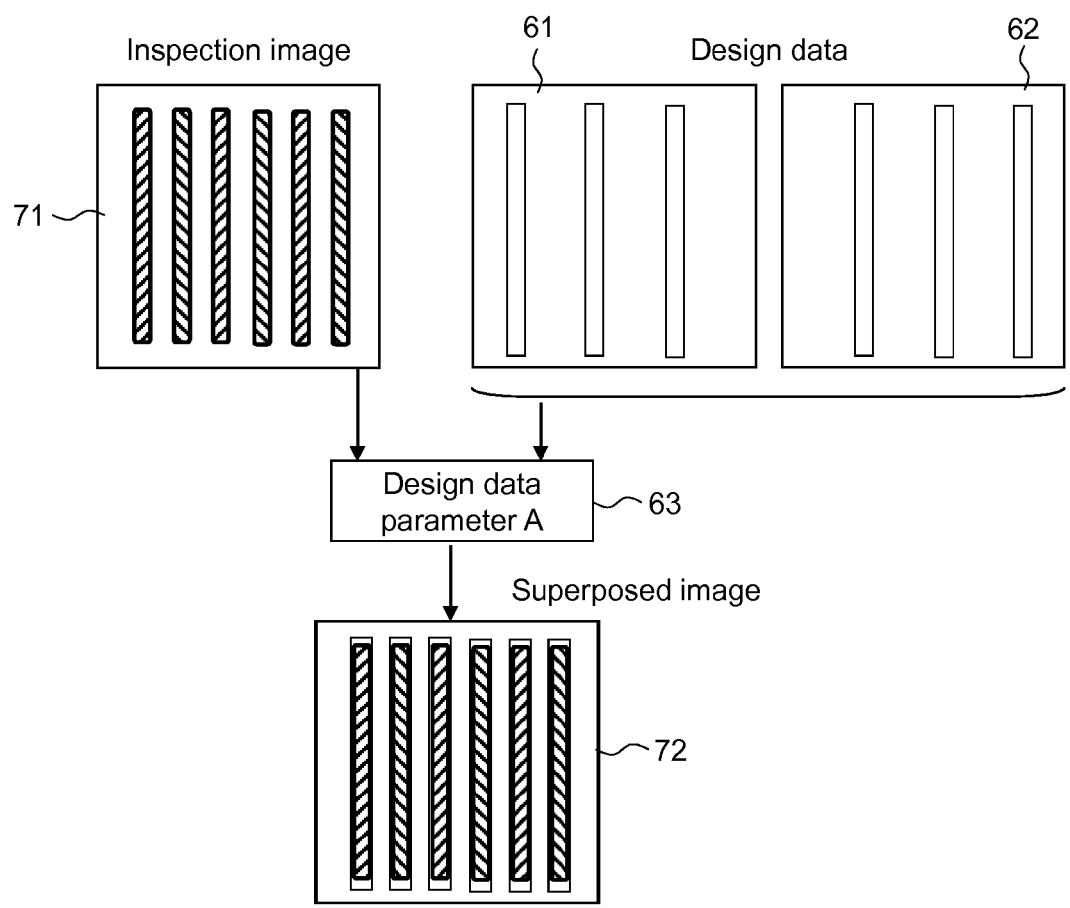
FIG. 8 illustrates a superposed display of layout data reflecting a parameter A of FIG. 7 and an inspection image including an ideal pattern.

FIG. 8 illustrates the superposed display of the layout data reflecting the parameter A of FIG. 7 and the inspection image including an ideal pattern. The inspection image 71 includes a pattern generated with design ideal values. The parameter A (63) is a parameter for executing the superposition with design ideal values of the two patterns 61 and 62. Thus, with respect to the pattern generated with the design ideal values, when the superposition is performed with the parameter A (63) of the design ideal values of the two patterns 61 and 62, an image 72 in which the inspection image and the layout data are accurately superposed can be obtained.

Figure 9:
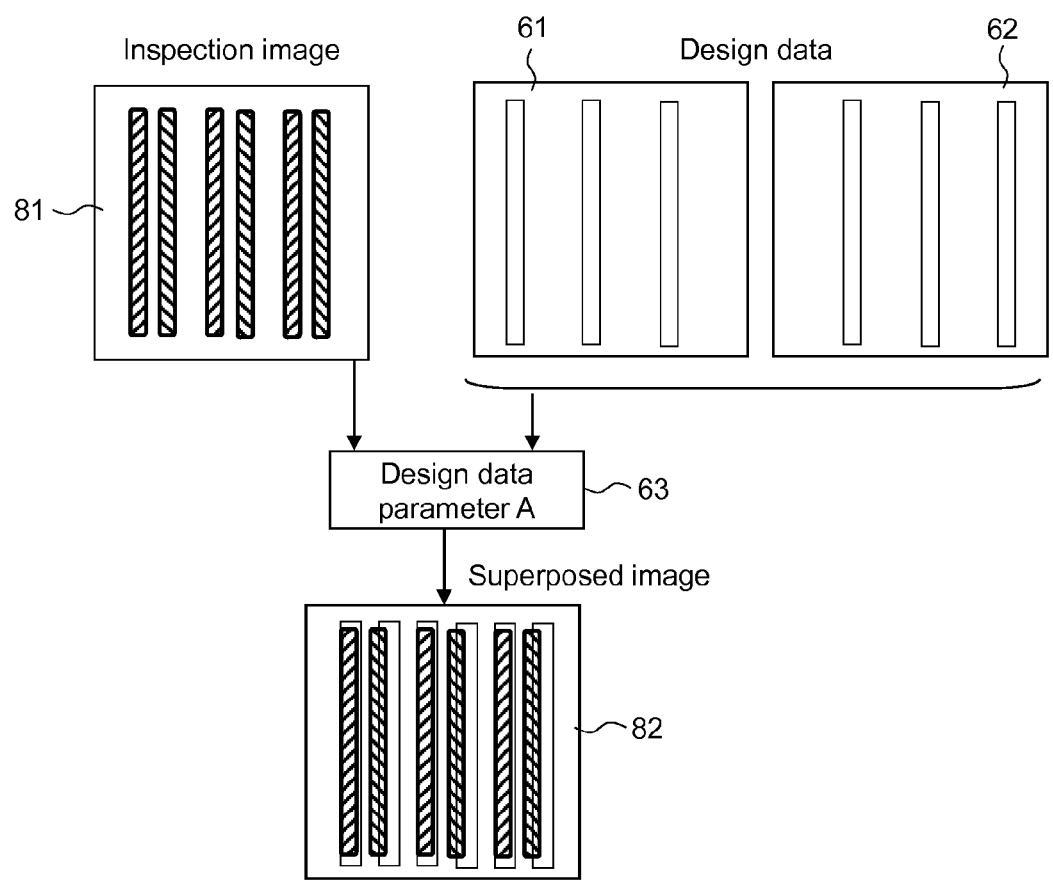
FIG. 9 illustrates a superposed display of the layout data reflecting the parameter A of FIG. 7 and an inspection image including a pattern having an error.

FIG. 9 illustrates the superposed display of the layout data reflecting the parameter A of FIG. 7 and the inspection image including a pattern having an error. In multiple patterning, a displacement may be caused between the two patterns 61 and 62 due to an error in an actual process step. With respect to a pattern 81 having an error, if the superposition is performed with the parameter A (63) of the design ideal values of the two patterns 61 and 62, a display misalignment may be produced, making it difficult to perform the defect parsing and classification process.

Figure 10:
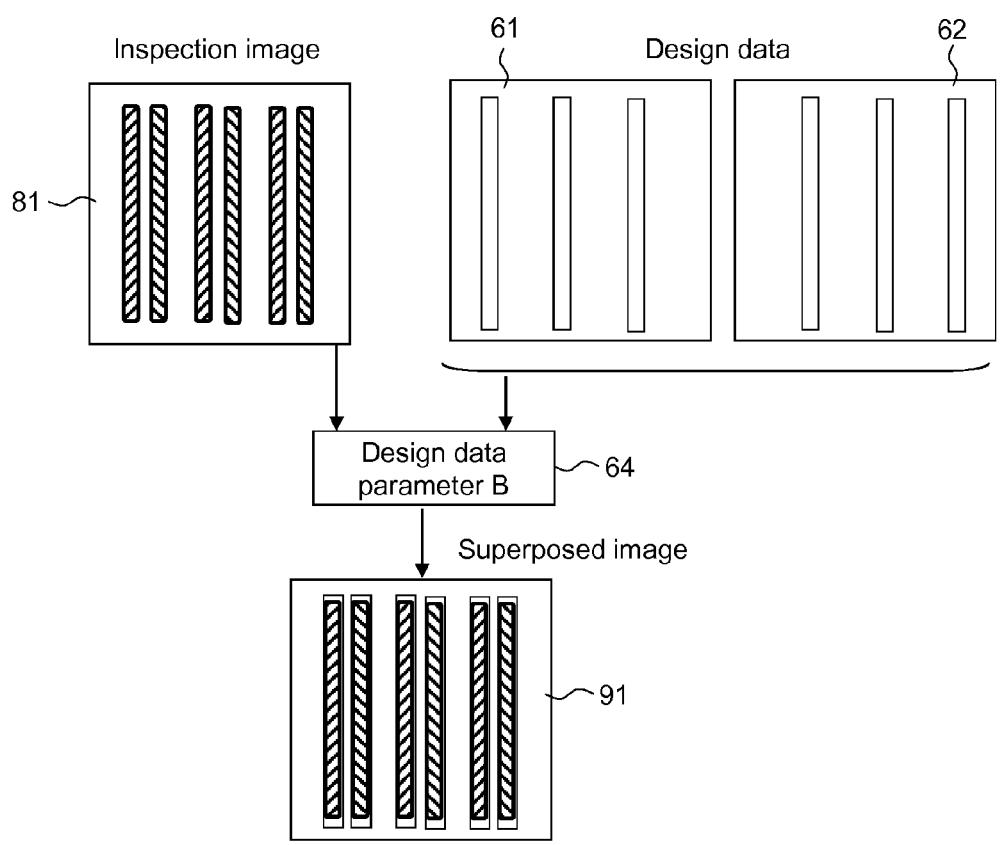
FIG. 10 illustrates a superposed display of layout data reflecting a parameter B of FIG. 7 and the inspection image including the pattern having an error.

FIG. 10 illustrates the superposed display of the layout data reflecting parameter B of FIG. 7 and the inspection image including the pattern having an error. The parameter B (64) includes a parameter, as superposition information, of the amount of offset of the two patterns 61 and 62. With respect to the pattern 81 having an error, the parameter B (64) including the amount of offset of the two patterns 61 and 62 is used, whereby an image 91 in which the inspection image and the layout data are accurately superposed can be obtained. The amount of offset may be determined from the actual inspection image pattern, or determined from the amount of shift in the layout data display as a function of the defect classification equipment 6.

Thus, in multiple patterning, the interval of a pattern generated in each process step may not correspond to the design ideal value due to a position alignment error and the like of the manufacturing device. According to the present embodiment, even in such a case, the information about the amount of offset is used as superposition information with respect to the inspection image, whereby alignment with the actual inspection image pattern can be achieved.

CONCLUSION

According to the present embodiment, the defect classification equipment 6 is provided with the storage unit 122, the processing unit 121, and the user interface 126 including the display device. The storage unit 122 stores the design data file 28 and the defect information data file 29. The processing unit 121 displays the defect image and the layout data on the display device of the user interface 126 in a superposed manner. Thus, with respect to a layer including a defect portion, the layout image of another layer (such as a lower layer) that could be a defect factor can be selected as needed from the divided layout data, collated, and displayed, enabling the operator to confirm the presence or absence of the influence of the other layer on the defect. For example, when the inspection object layer is a poly-Si layer, information as to whether a layer under the defect is an N-type or P-type active area (impurity injected area) or a non-active area can be obtained. Based on the information, it can be determined, for example, whether the defect is a systematic defect. The state of displacement (error) of the active area or non-active area can also be learned, enabling a detailed analysis of the characteristics of the defect. Further, based on the layout data, the defect can be classified on the basis of the position information of a cell, a peripheral circuit, or a dummy pattern and the like.

Further, according to the present embodiment, the design database server 5 stores the design data 9 in a divided manner. The design data 9 is divided for each layer of the manufacturing step, or, when one layer forms a pattern by a plurality of process steps, the design data 9 is divided for each process step. Thus, the storage unit 122 stores the divided design data 9 as the design data file 28, and the processing unit 121 can execute the superposed display of the defect image and the layout data using the divided layout data. Accordingly, the defect analysis and parsing process can be implemented easily and efficiently even for large-scale design layout data.

Further, according to the present embodiment, the storage unit 122 stores, as the superposition information concerning the superposition of layout data, information such as the amount of offset between layers, and the amount of pattern offset in multiple patterning. The processing unit 121 displays the layout data reflecting the superposition information and the inspection image on the display device in a superposed manner. The layers or patterns generated in each step may in some cases not correspond to design ideal values due to position alignment error and the like of the manufacturing device. In such cases, too, alignment with the actual inspection image pattern can be achieved by using the information of the amount of offset as the superposition information with respect to the inspection image. Thus, the defect analysis and parsing process can be implemented by considering the manufacturing error in the actual manufacturing process.

While the embodiment of the present invention has been described, the present invention is not limited to the foregoing embodiment, and various modifications or changes may be made based on the technical concept of the present invention.

For example, while in the configuration of the foregoing embodiment, the amount of offset of layers or patterns (error information) is used as the superposition information, other information, such as pattern width information, may be used. In this way, the defect analysis and parsing process can be performed with not only the position of the actual inspection image pattern but also the width of the pattern aligned.

In the above example of FIG. 5, the layout data of the lower layer of the inspection object is acquired for the superposed display, the present invention is not limited to such example. In another example, the processing unit 121 may acquire the layout data of an upper layer (next step) of the layer having a defect, and display the layout data for the next step with the inspection image in a further superposed manner. In this case, the operator can analyze to what extent a manufacturing error can be permitted in the next step. That is, the operator is enabled to analyze the likelihood of the next step in advance.

While in the configuration of the foregoing embodiment, the processing unit 121 acquires the defect image and the layout data from the design data file 28 and the defect information data file 29 in the storage unit 122, the present invention is not limited to such configuration. For example, the processing unit 121 may be configured to receive the layout data directly from the design database server 5. Alternatively, the processing unit 121 may be configured to receive the defect image directly from the defect data processing device 4.

The configuration of the foregoing embodiment may be realized by hardware by designing a part or all of the configuration on an integrated circuit, for example. The present invention may be realized by a software program code for realizing the functions of the embodiment. In this case, a non-transitory computer readable medium having the program code recorded therein may be provided to an information processing device (such as the defect classification equipment 6), and the information processing device (or a CPU or an operating unit) may read the program code stored in the computer readable medium. In this case, the program code per se read from the computer readable medium realizes the functions of the embodiment, where the program code per se or the computer readable medium storing the code constitutes the present invention. Examples of the non-transitory computer readable medium for supplying such program code include a flexible disc, a CD-ROM, a DVD-ROM, a hard disk, an optical disc, a magnetooptic disc, a CD-R, a magnetic tape, a non-volatile memory card, and a ROM.

Based on the instruction of the program code, some or all of actual processes may be performed by the operating system (OS) and the like running on the defect classification equipment 6, so that the functions of the embodiment can be realized by the processes. Further, after the program code read from the storage medium is written to a storage unit such as a memory in the defect classification equipment 6, some or all of the actual processes may be performed by the CPU (or operating unit) and the like of the defect classification equipment 6 based on the instruction of the program code, so that the functions of the embodiment can be realized by the processes.

Further, the software program code for realizing the functions of the embodiment may be delivered via a network, stored in the storage unit of the defect classification equipment 6 or the storage medium such as a CD-RW or a CD-R, and then read and executed by the CPU (or operating unit) of the defect classification equipment 6 during use.

Finally, it should be understood that the processes and technologies described herein are not essentially associated with any specific device, and may be implemented by any appropriate combination of components. Various types of general-purpose devices may be used in accordance with the teaching described herein. It may be realized that the method steps described herein may be beneficially executed by constructing a dedicated device. While the present invention has been described with reference to specific examples, the description is for illustrative purposes and not for limitation in every respect. It may readily occur to those skilled in the relevant field that the present invention may be implemented by a number of combinations of appropriate hardware, software, and firmware. For example, the program code for realizing the functions described in the present embodiment may be implemented by a wide range of programs or script languages, such as assembler, C/C++, perl, Shell, PHP, ad Java (registered trademark).

The control lines and information lines shown in the drawings are those considered necessary for description and may not necessarily represent all of control lines or information lines found in a product. All of the configurations may be mutually connected.

REFERENCE SIGNS LIST

1 Semiconductor defect inspection system
2 Defect inspection device
3 Review device
4 Defect data processing device
5 Design database server
6 Defect classification equipment
7 Network
8 Clean room
120 Communication unit
121 Processing unit
122 Storage unit
123 Layout conversion operating unit
124 Classification determination definition unit
125 Defect determination unit
126 User interface

What is claimed is:

1. Semiconductor defect classification equipment for classifying a defect in a semiconductor wafer, the equipment comprising:
a display unit;
a storage unit that stores (i) an inspection image including an inspection object portion on the semiconductor wafer, (ii) design data used to manufacture the semiconductor wafer including a plurality of manufacturing steps, (iii) a plurality of layout data of the design data divided for each of the manufacturing steps, each manufacturing step including at least two patterning processes to be performed on a same layer, the at least two patterning processes including a first patterning process of forming a first pattern on the semiconductor wafer and a second patterning process of forming a second pattern on the semiconductor wafer after performing the first patterning process, and the second pattern being different from the first pattern, and (iv) superposition information including error information between the first pattern formed by the first patterning process of the at least two patterning processes and the second pattern formed by the second pattering process of the at least two patterning processes; and
a processing unit that displays the inspection image and the design data on the display unit,
wherein:
the processing unit acquires at least one layout data and the inspection image from the storage unit, and
the processing unit displays the at least one layout data in which a relative positional relationship between layout design information used to manufacture the first pattern and layout design information used to manufacture the second pattern is adjusted based on the superposition information, and the inspection image on the display unit in a superposed manner.

2. The semiconductor defect classification equipment according to claim 1, further comprising an input unit for a user to select the at least one layout data,
wherein the processing unit displays the at least one layout data selected by the input unit and the inspection image on the display unit in a superposed manner.

3. The semiconductor defect classification equipment according to claim 1, wherein the processing unit acquires the at least one layout data corresponding to a next manufacturing step of the semiconductor wafer as an inspection object, and displays the at least one layout data corresponding to the next step and the inspection image in a further superposed manner.

4. A non-transitory computer readable medium having recorded therein a program for causing an information processing device provided with a display unit, a storage unit, and an processing unit to execute a process for classifying a defect in a semiconductor wafer,
wherein:
the storage unit stores (i) an inspection image including an inspection object portion on the semiconductor wafer, (ii) design data used to manufacture the semiconductor wafer including a plurality of manufacturing steps, (iii) a plurality of layout data of the design data divided for each of the manufacturing steps, each manufacturing step including at least two patterning processes to be performed on a same layer, the at least two patterning process including a first patterning process of forming a first pattern on the semiconductor wafer and a second patterning process of forming a second pattern on the semiconductor wafer after performing the first patterning process, and the second pattern being different from the first pattern, and (iv) superposition information including error information between the first pattern formed by the first patterning process of the at least two patterning processes and the second pattern formed by the second pattering process of the at least two patterning processes; and
the program causes the processing unit to execute
a process of acquiring at least one layout data and the inspection image from the storage unit; and
a process of displaying the at least one layout data in which a relative positional relationship between layout design information used to manufacture the first pattern and layout design information used to manufacture the second pattern is adjusted based on the superposition information, and the inspection image on the display unit in a superposed manner.

* * * * *